United States Patent
Benner et al.

(10) Patent No.: US 10,191,131 B2
(45) Date of Patent: Jan. 29, 2019

(54) MEDICAL IMAGING APPARATUS HAVING MULTIPLE SUBSYSTEMS, AND OPERATING METHOD THEREFOR

(71) Applicant: Siemens Aktiengesellschaft, Munich (DE)

(72) Inventors: Thomas Benner, Erlangen (DE); Swen Campagna, Engelthal (DE); Thorsten Feiweier, Poxdorf (DE); Bernd Kuehn, Uttenreuth (DE); Peter Speier, Erlangen (DE)

(73) Assignee: Siemens Healthcare GmbH, Erlangen (DE)

( * ) Notice: Subject to any disclaimer, the term of this patent is extended or adjusted under 35 U.S.C. 154(b) by 588 days.

(21) Appl. No.: 14/870,035

(22) Filed: Sep. 30, 2015

(65) Prior Publication Data
US 2016/0091588 A1   Mar. 31, 2016

(30) Foreign Application Priority Data

Sep. 30, 2014   (DE) .................. 10 2014 219 785

(51) Int. Cl.
*G01V 3/00*   (2006.01)
*G01R 33/54*  (2006.01)
(Continued)

(52) U.S. Cl.
CPC .......... *G01R 33/543* (2013.01); *A61B 5/055* (2013.01); *G01R 33/4835* (2013.01)

(58) Field of Classification Search
USPC ....................................................... 324/309
See application file for complete search history.

(56) References Cited

U.S. PATENT DOCUMENTS 6,515,478 B1   2/2003   Wicklow et al.
7,218,113 B2   5/2007   Feiweier et al.
(Continued)

OTHER PUBLICATIONS

De Graaf et al., "Dynamic Shim Updating (DSU) for Multi-Slice Signal Acquisition," Proc. Intl. Soc. Mag. Reson. Med., vol. 10 (2002).

(Continued)

*Primary Examiner* — Rodney Fuller
(74) *Attorney, Agent, or Firm* — Schiff Hardin LLP

(57) ABSTRACT

In a method for operating a medical imaging apparatus having subsystems, a control protocol assigned to a scan sequence to be performed is provided to a control computer that determines sequence control data for the control protocol, which define different functional subsequences of the scan sequence. Different effective volumes are assigned to each functional subsequence, and current ambient conditions of the apparatus are determined for the sequence control data and associated effective volumes, for a series of states of physiological processes that occur during the scan sequence. Control signals for the scan sequence are determined from the sequence control data, the effective volumes and the current ambient conditions per observed state, that optimize the functional subsequences of the scan sequence locally. During the scan, at least one current state of the observed physiological processes is determined and the control signals used for the ongoing scan are determined from the stored control signals, dependent on the at least one current state.

14 Claims, 5 Drawing Sheets

(51) Int. Cl.
*A61B 5/055* (2006.01)
*G01R 33/483* (2006.01)

(56) References Cited

U.S. PATENT DOCUMENTS

| | | | |
|---|---|---|---|
| 8,111,069 B2 | 2/2012 | Feiweier | |
| 2005/0033156 A1* | 2/2005 | Kruger | G01R 33/243 |
| | | | 600/410 |
| 2009/0033328 A1* | 2/2009 | Feiweier | G01R 33/54 |
| | | | 324/309 |
| 2010/0182007 A1* | 7/2010 | Dornhaus | G01R 33/243 |
| | | | 324/309 |
| 2010/0286802 A1* | 11/2010 | Feiweier | G01R 33/54 |
| | | | 700/90 |
| 2011/0172515 A1 | 7/2011 | Fautz et al. | |
| 2012/0217966 A1 | 8/2012 | Feiweier | |
| 2012/0249137 A1 | 10/2012 | Witschey et al. | |
| 2016/0091586 A1* | 3/2016 | Benner | G01R 33/543 |
| | | | 324/322 |

OTHER PUBLICATIONS

Meier et al., "Concomitant Field Terms for Asymmetric Gradient Coils: Consequences for Diffusion, Flow, and Echo-Planar Imaging," Magnetic Resonance in Medicine, vol. 60, pp. 128-134 (2008).

* cited by examiner

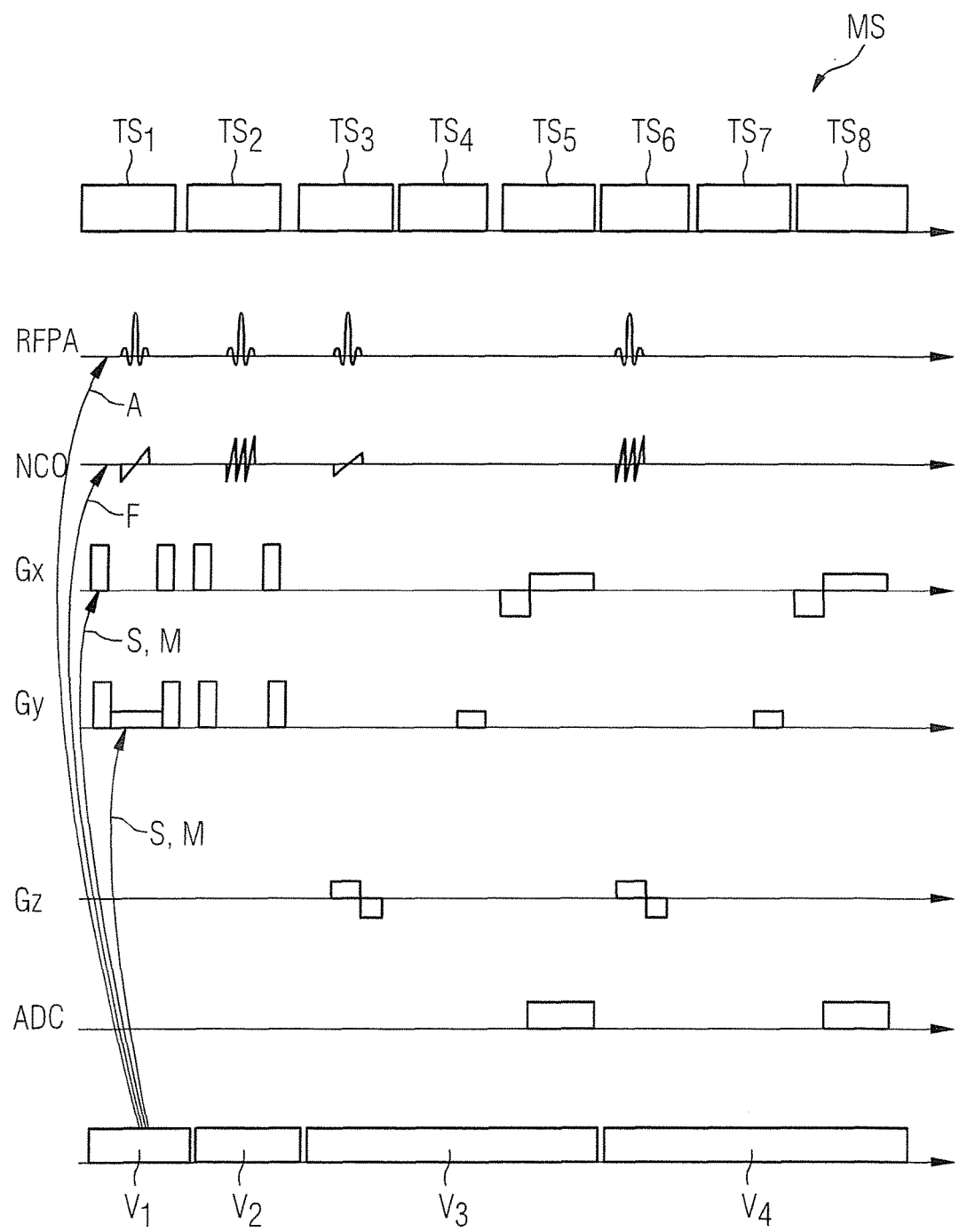

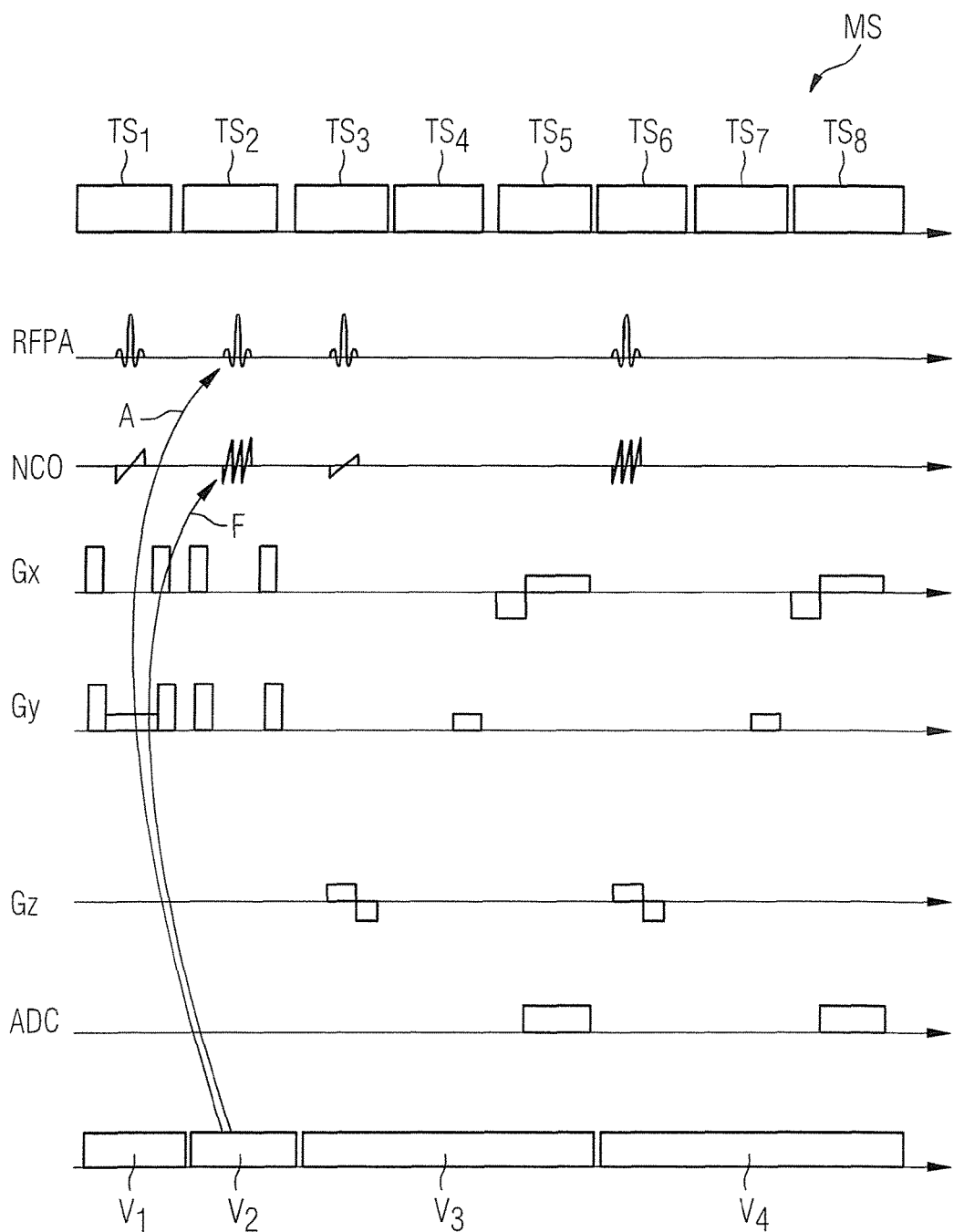

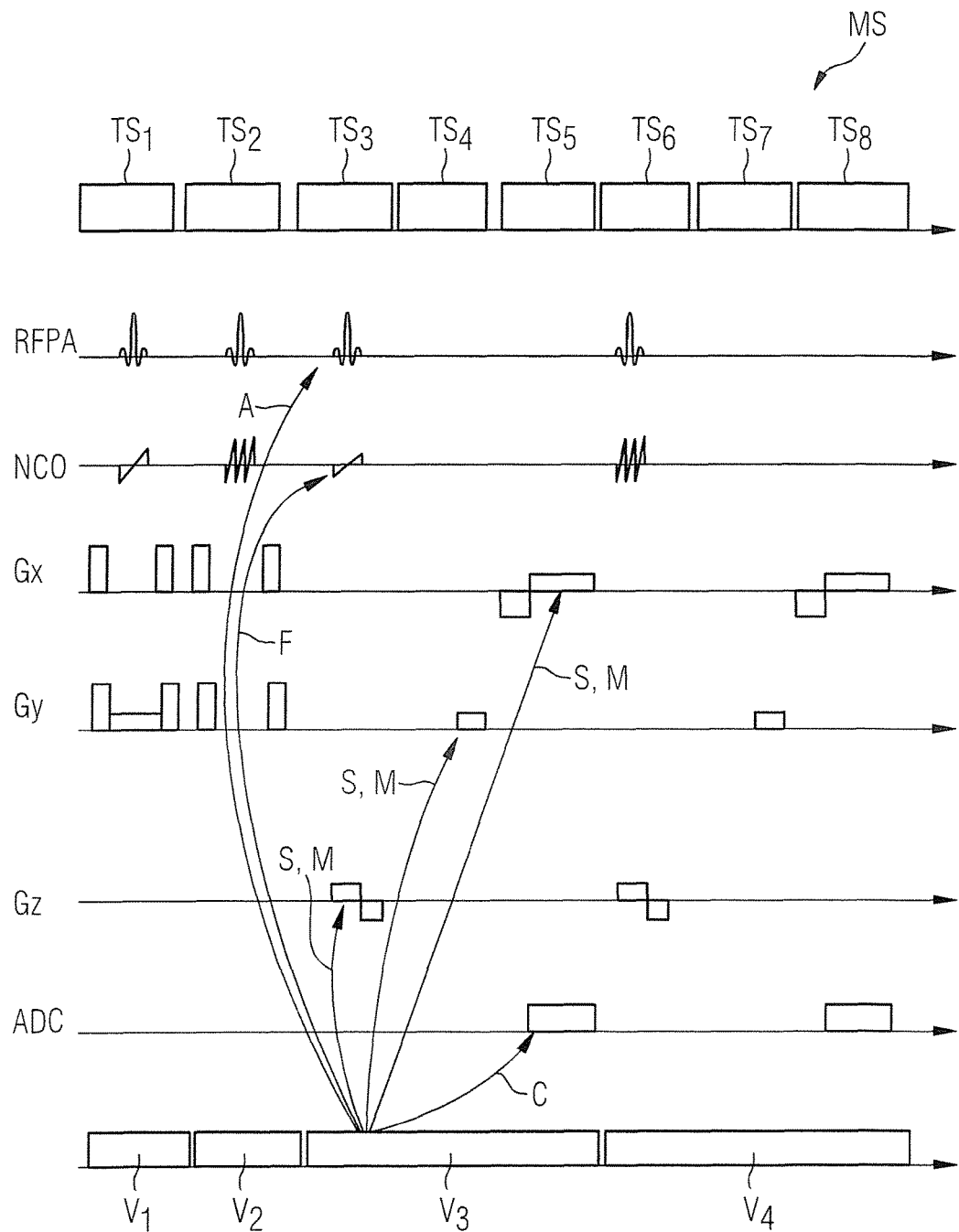

MEDICAL IMAGING APPARATUS HAVING MULTIPLE SUBSYSTEMS, AND OPERATING METHOD THEREFOR

BACKGROUND OF THE INVENTION

Field of the Invention

The invention concerns to the operation of a medical imaging examination apparatus having multiple subsystems, a corresponding medical imaging examination apparatus, and an associated electronically readable data carrier encoded with programming instructions for implementing such a method.

Description of the Prior Art

Medical imaging examination apparatuses such as magnetic resonance apparatuses and computed tomography apparatuses are complex systems with a large number of technical subsystems. These include, in a magnetic resonance apparatus, a basic field magnet system, a gradient system, a shim system and a radio frequency transmission system as well as a radio frequency receiving system.

In order to generate images or spectroscopic data from an examination object with a magnetic resonance apparatus, the examination object is positioned in the scanner in a strong homogeneous basic magnetic field, also known as the $B_0$ field, generated by the basic field magnet system with a field strength of 0.2 Tesla to 7 Tesla or more, so that the nuclear spins in the object align along the basic magnetic field direction. In order to trigger nuclear spin resonance, radio frequency excitation signals (RF pulses) are radiated into the examination object with suitable antennas of the radio frequency transmission system, so that the nuclear spin of particular atoms stimulated to resonance by this radio frequency field are tilted through a particular flip angle relative to the magnetic field lines of the basic magnetic field. The nuclear spin resonance that is triggered, i.e. the radio frequency signals (also "magnetic resonance signals") emitted during the precession of the nuclear spin are detected by the radio frequency receiving system, typically digitized, and normally stored as complex number values (if a spatial reference is given) in a "k-space matrix" as "k-space data". For example, in single-voxel spectroscopy scans (without spatial reference), the digitized data are stored as complex time signals, also known as "FID data". On the basis of the k-space data or FID data, MR images can be reconstructed or spectroscopic data can be determined. For spatial encoding of the scan data, rapidly switched magnetic gradient fields are overlaid on the basic magnetic field by the gradient system. The shim system is intended to homogenize the magnetic fields.

All these technical modules must be suitably operated in a coordinated way by a control system. The adjustment and switching of the individual subsystems necessary for a particular imaging process must be undertaken by the control system at the right time point in each case. Typically, the volume to be imaged within an imaging sequence is recorded in subvolumes, for example, in 2-D imaging, in multiple slices or, in 3-D imaging, in multiple "slabs". The subvolumes recorded in this way are then assembled into an overall volume. A further definition of subvolumes can be given as "regions of interest" (ROI) or "volumes of interest" (VOI) defined, for example, by the operator. Furthermore, in magnetic resonance systems, additional subvolumes arise when determining local saturation regions or local preparation or labeling pulses.

As mentioned above, sequence control data are transmitted to the control device for coordinated control, typically based on a "scan protocol". These sequence control data define different functional subsequences of a complete scan sequence. In a magnetic resonance recording, for example, a first subsequence may be a pulse sequence in order to achieve a saturation locally in a particular region. Further subsequences can contain, for example, particular preparation pulses and yet further subsequences serve for successive excitation and for receiving the magnetic resonance signals in different slices or slabs.

Typical methods based on MR technology, such as tomographic imaging (MRT—magnetic resonance tomography) or spectroscopy (MRS—magnetic resonance spectroscopy) require "benign" ambient physical conditions in order to ensure the best possible quality in the data recorded. For example, this relates to the spatial homogeneity, temporal stability and the absolute accuracy of the relevant magnetic fields and radio frequency fields, that is, the main magnetic field ($B_0$) and the gradient and radio frequency fields ($B_1$).

Conventionally, deviations from ideal ambient conditions can at least partially be compensated for, for example, by system-specific settings known as "tune-ups", in particular with regard to eddy current-induced dynamic field disruptions or gradient sensitivities or by examination object-specific settings, particularly in relation to susceptibility-related static field disruptions or spatial variations of the radio frequency field. However, the compensation settings specified before the beginning of a scan conventionally remain valid throughout the entire scan ("static" adjustment).

For spatially variable ambient conditions that cannot be entirely compensated, this entails a compromise for data quality.

De Graaf et al. describe in "Dynamic Shim Updating (DSU) for Multi-Slice Signal Acquisition", Proc. Intl. Soc. Mag. Reson. Med. 10, p. 536, 2002, a rudimentary form of a dynamic adjustment of the shim currents of the field coils for the B0 shim in functional multi-slice MR imaging. For this purpose, a firm field determination sequence is created for determining spatial field changes of first or higher orders which must be exactly matched to the corresponding parameters (e.g. slice positions and orientations) of the desired imaging sequence. The field determination sequence records the data necessary for field determination and analyzes them in order to calculate optimized shim currents (of first or higher order) therefrom for each slice to be scanned with the imaging sequence. Subsequently, the imaging sequence is started with the optimized shim currents. The user needs to watch very closely for consistency between the imaging sequence and the field determination sequence since, otherwise, inconsistencies can lead to a worsening of the image quality. Therefore, for each imaging sequence and each change of such a sequence, a new field determination sequence must be created and carried out before the scan with the imaging sequence. These methods are therefore very complex and difficult for the user to combine with other, for example static, adjustments since interactions between different parameters cannot be taken into account or only to a limited extent. If statically adjusted parameters are changed, this can have effects on the optimum dynamic settings of the shim currents and a new field determination sequence and calculation of the optimized shim currents would have to be carried out. Furthermore, the optimization is restricted to the slices of the imaging sequence. Smaller volumes, for example, regional saturation volumes are not taken into account here.

In DE 10 2009 020 661 B4 also, a method is described with which parameters of a scan sequence, for example, within magnetic resonance technology can be adapted at the run time of the scan sequence. Furthermore, it is described therein that different functional subsequences are typically associated with different effective volumes. I.e. for each subsequence, a different subvolume of the overall scan volume is relevant. Due to the determination of the parameters at run time, it can however occur that, in the time available which is limited due to the already running scan sequence, no useful parameters can be determined. In this event, either the scan as a whole can be terminated or sub-optimum, static parameters can be utilized.

SUMMARY OF THE INVENTION

An object of the present invention is to provide a method for the operation of a medical imaging examination apparatus that has multiple subsystems, and a control computer that controls the subsystems in a coordinated manner in order to carry out a scan sequence, a medical imaging examination apparatus and an associated electronically readable data carrier, which enable reliable adaptation of sequence control data to existing ambient conditions (adjustment) in a user-friendly and time-optimized manner and overcomes the above-mentioned disadvantages of conventional methods.

The invention is based, inter alia, on the insight that for scans in which the volume of the examination object relevant for the signal excitation and the data reception changes during the scan, the quality of the data can be significantly improved by a dynamic optimization of the compensation settings for the currently relevant volumes. This applies, for example, for two-dimensional multi-slice imaging, multi-voxel spectroscopy (e.g. in conjunction with successive localized excitation) or on use of diverse magnetization preparations (e.g. fat suppression, regional saturation, inversion, markings, etc.). A further underlying consideration is that particular ambient conditions, for example, the spatial tissue distribution and thus local basic magnetic fields B0 and radio frequency fields B1 depend on states of physiological processes such as breathing, heartbeat, pulse and other movements, for example, of the joints of the examination object.

The above object is achieved by a method according to the invention for the operation of a medical imaging examination device having multiple subsystems and a control computer that controls the subsystems in a coordinated manner in order to execute a scan sequence, that includes transferring a control protocol assigned to a scan to be performed to the control computer, determining sequence control data of relevance for the control protocol that define different functional subsequences of a scan sequence belonging to the control protocol, assigning different effective volumes to each functional subsequence, determining ambient conditions of the medical imaging examination device that affect the determined relevant sequence control data and associated effective volumes, for a series of states of physiological processes that are expected to occur during the scan sequence, calculating and storing control signals for the scan sequence on the basis of the determined sequence control data, the effective volumes and the current ambient conditions determined for each determined state, with the functional subsequences of the scan sequence being optimized locally at least with regard to a subregion of the associated effective volume thereof, starting a scan in accordance with the control protocol, and during the scan, determining at least one current state of the observed physiological processes and determining the control signals used for the ongoing scan on the basis of the stored control signals, taking account of the at least one current state.

With the method according to the invention and the central determination therein of control signals even before the actual scan, it is made possible to use a dynamic adjustment and thus optimization of control signals reliably, in a user-friendly way and time-optimized, including in routine clinical practice. Herein, restriction in a targeted manner to subregions in a volume of interest of the examination object is possible, and this has a positive effect on the computation time and on the quality of the examination results. By the restriction to respective relevant sequence control data and the determination and making available of the optimized control signals, the data flow is optimized and therefore can be easily integrated into existing workflows. By the improved possibilities for adapting the control signals, it is also possible to build less expensive hardware into the medical imaging examination apparatuses used, and thereby to manufacture these devices more economically, since any sub-optimum ambient conditions due to the hardware can be compensated for with the method. Thus, with the method according to the invention, an optimized integration of the scans, evaluations and uses employed for determining the optimized control signals into the technical sequence of the scan of the data from the examination object through the control protocol is provided.

In the inventive method, it is not necessary, as in the prior art, for a user to ensure the consistency of different scan protocols, for example, protocols for adjustment scans for determining ambient conditions and from the actual scan. Rather, established adjustment scans can be used without a user having to parameterize them first.

By the determination of control signals according to the invention for different states of physiological processes occurring, a consistent quality of the scan data can be achieved even under temporal variation of the ambient conditions depending on the physiological processes. Herein, at most a slight intervention into the ongoing scan is necessary in order to determine current states of the physiological processes.

A medical imaging examination apparatus according to the invention with multiple subsystems has a control computer configured to implement the method according to the invention, wherein the control computer is configured to control the subsystems in a coordinated manner for executing a scan sequence on the basis of sequence control data, wherein the sequence control data define various functional subsequences of the scan sequence with which different effective volumes are associated.

A non-transitory, electronically readable data carrier according to the invention has electronically readable control information (programming instructions) stored thereon, so that, when the data carrier is loaded in a control computer of a medical imaging examination apparatus, the programming instructions cause the control computer to implement the method according to the invention.

The advantages and details described above with respect to the method apply to the medical imaging examination apparatus, and the electronically readable data carrier.

BRIEF DESCRIPTION OF THE DRAWINGS

FIG. 3 is a simplified exemplary embodiment of a scan sequence with multiple subsequences and their associated effective volumes, with a representation of the parameters for the individual subsystems optimized for the first subsequence to the first effective volume.

FIG. 4 shows the scan sequence with the individual subsequences and associated effective volumes as in FIG. 3, but with a representation of the parameters of the subsystems optimized for the second subsequence to the second effective volume, FIG. 5 shows the scan sequence with the individual subsequences and associated effective volumes as in FIG. 3, but with a representation of the parameters of the subsystems optimized for the third effective volume.

DESCRIPTION OF THE PREFERRED EMBODIMENTS

Figure 1:
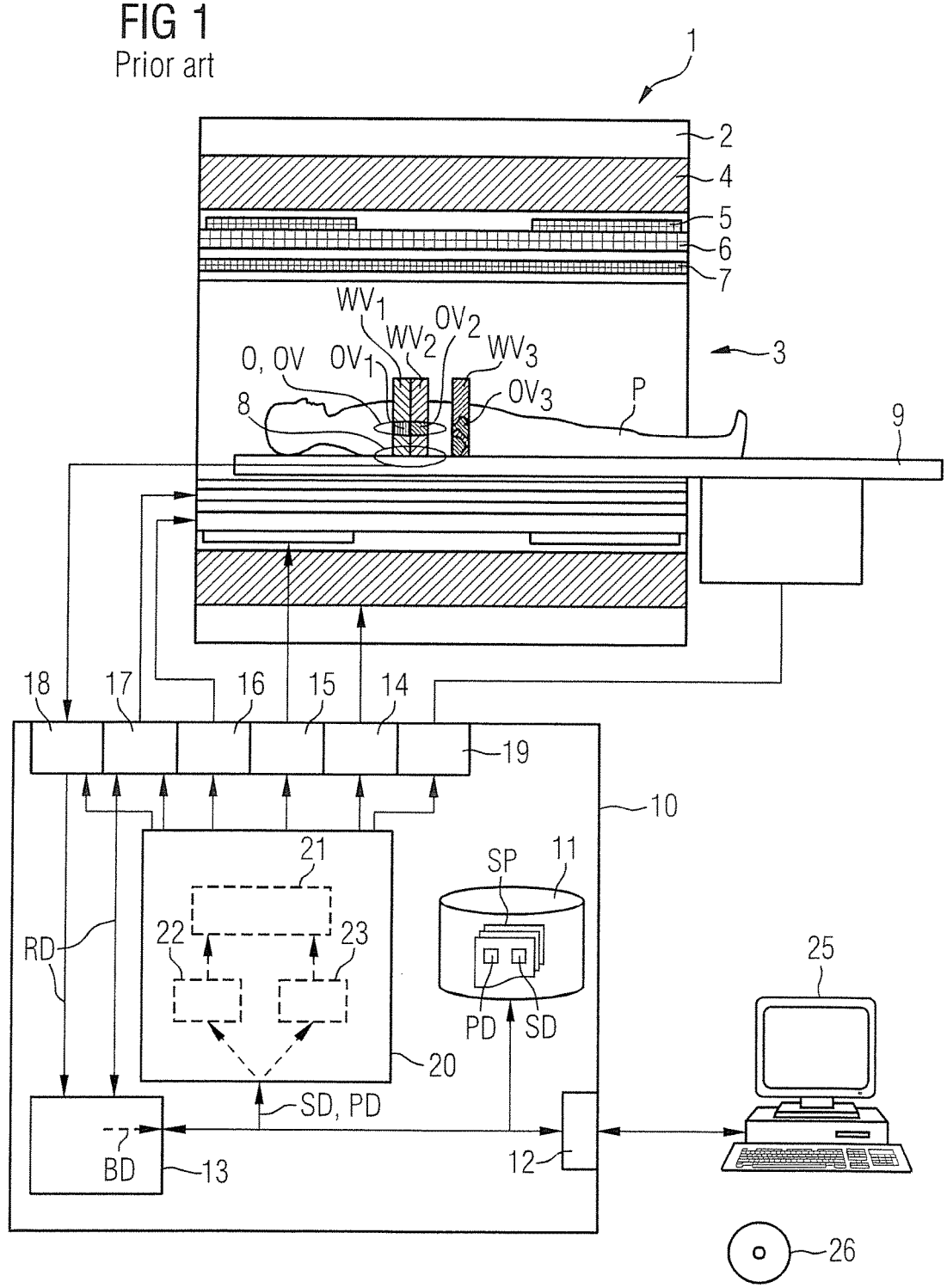
FIG. 1 schematically illustrates a known medical imaging examination apparatus in the form of a magnetic resonance apparatus, that can implement the invention.

FIG. 1 shows a basic schematic form of a medical imaging examination apparatus 1 that although the basic components are known, can be configured according to the invention. The apparatus includes the actual magnetic resonance scanner 2 with an examination space 3 or patient tunnel situated therein. A table 9 can be moved into this patient tunnel 3 through various positions so that an examination object, e.g. a patient P or test subject lying thereon can be placed during an examination at a particular position within the magnetic resonance scanner 2 relative to the magnetic system and the radio frequency system arranged therein and is also displaceable between different positions during a scan. It should be mentioned at this point that the exact construction of the magnetic resonance scanner 2 is not essential. Thus, for example, a cylindrical system with a typical patient tunnel can be used, but also a C-arm-shaped magnetic resonance device which is open at one side.

Basic components of the magnetic resonance scanner 2 are a basic field magnet 4, a number of shim coils 5 and magnetic field gradient coils 6 as well as a whole-body radio frequency coil 7. The reception of magnetic resonance signals induced in the examination object can take place by the whole body coil 7, with which typically the radio frequency signals for inducing the magnetic resonance signals are also emitted. It is also possible to receive these signals, for example, with local coils 8 placed on or under the patient. All of these components are known to those skilled in the art and are shown only schematically in FIG. 1.

The individual components are controlled by a control computer 10, which is shown here in the form of a combined block. This can be a control computer that can be composed of a number of individual computers, possibly spatially separated and connected to one another by suitable cables or the like. This control computer 10 is connected, via a terminal interface 12, to a terminal 25, via which an operator can control the entire system 1. The terminal interface 12 should be understood as meaning any connection of input devices, such as a mouse and/or keyboard, and display devices, for example a screen or monitor of the terminal 25 to the control computer 10.

This control computer 10 has, inter alia, a basic magnetic field control apparatus 14 that monitors the cooling of the basic field magnet, a shim coil control apparatus 15, and a gradient coil control apparatus 16. The whole body coil 7 is controlled by a radio frequency transmission/receiving unit 17. The radio frequency transmitting/receiving unit 17 has, for example, a radio frequency pulse amplifier for amplification and shaping of the radio frequency pulses and an NCO with which the frequency and phase position of the radio frequency pulses can be stipulated. With a further radio frequency receiving unit 18, signals detected by local coils 8 are read out. This radio frequency receiving unit (processor) 18 can include, for example, a coil selection unit in order to select the relevant local coil from among multiple local coils that are available, and an NCO for setting the frequency and phase position. A patient table control unit 19 serves to control the table 9.

The basic field magnet 4, together with its control apparatus 14, the basic magnetic field system 4, 14, the shim coils 5 together with the associated control apparatus 15, the shim system 5, 15, the magnetic field gradient coils 6 with the associated control apparatus 16, the gradient system 6, 16, the radio frequency coils 7 together with their radio frequency transmission/receiving unit 17, form a radio frequency transmission/receiving system 7, 17 and the local coils 8 together with their radio frequency receiving unit 18 form a further radio frequency receiving system 8, 18.

All the control apparatuses 14, 15, 16, 19 and the radio frequency transmitting and/or receiving units 17, 18 are controlled in a coordinated manner by a central control computer 20 so that the basic magnetic fields, gradient fields and radio frequency pulses required for the execution of a scan are output-synchronized, the shim coils are correctly set and the table 9 is in the correct position. Furthermore, it must be ensured that, at the relevant time point, the signals are read out at the local coils 8 by the radio frequency receiving unit 18 and any signals at the whole body coil 7 are read out by the radio frequency transmitting/receiving unit 17 and further processed in an appropriate manner.

The signals or raw data RD acquired in this way are then passed on to an image reconstruction unit 13 in which the desired magnetic resonance image data or spectroscopic data BD are reconstructed in order then to present them on the screen of the terminal 25 or to store them in a memory 11.

The magnetic resonance scanner 2 of this type and the associated control computer 10 also have or can have a number of further components that will not be discussed in detail herein. For example, the examination apparatus 1 can be coupled, via a suitable interface, to a network, for example, a radiological information system (RIS) in order to receive control protocols that can be used in the apparatus 1 or, for example, to transmit magnetic resonance images generated by the apparatus 1, to save them in external mass storage units or to transfer them to diagnosis stations or printers or the like.

The generation of the control signals for the individual control apparatuses 14, 15, 16, 19 and the radio frequency transmitting and/or receiving units 18, 17 by the central control computer 20 is accomplished via a control signal generating module 21, realized in the form of software, in a processor of the control computer 10 that generates the control signals ST on the basis of sequence control data SD that define the different subsequences of the complete scan sequence. An example of a scan sequence composed of multiple subsequences will be described below with reference to FIGS. 3 to 5. The sequence control data SD are typically set within control protocols SP that characterize the scan protocol of the scan to be carried out and can be stored for the apparatus 1 in a memory 11. A control protocol SP of this type contains all the control data necessary for the smooth execution of a particular scan sequence. The operator can select a protocol of this type SP for a scan to be carried out, by a suitable user interface via the terminal 25 and then have the scan performed fully automatically on the basis of this control protocol SP. However, it is also possible for the operator to call and modify a control protocol SP in order to carry out specific scans. It is also possible to select control protocols SP via a further network interface (not shown) on other computers, particularly from the manufacturer of the magnetic resonance system or made available by specialist service providers involved in the development of control protocols.

As described in detail above, it is useful for the achievement of the best possible image quality if the individual subsystems are controlled for a particular subsequence such that they are optimized to the effective volume essential for the particular subsequence or a particular part thereof. This has conventionally been achieved by the developer of a control protocol making account, in advance, of which effective volume is relevant for which subsequence, and then accordingly modifying the sequence control data or the parameters for the subsystems in the control protocol, so that with the subsequence, optimization is achieved in the defined effective volume.

The method described herein can also exist in the form of a computer program that implements the method on a control computer 10 when it is carried out on the control computer 10. An electronically readable data carrier 26 with electronically readable control information stored thereon can also be provided, the control information including at least one computer program written thereon and being configured such that, upon loading of the data carrier 26 into a control computer 10 of a medical imaging examination apparatus 1, the control information carries out a method as described.

Figure 2:
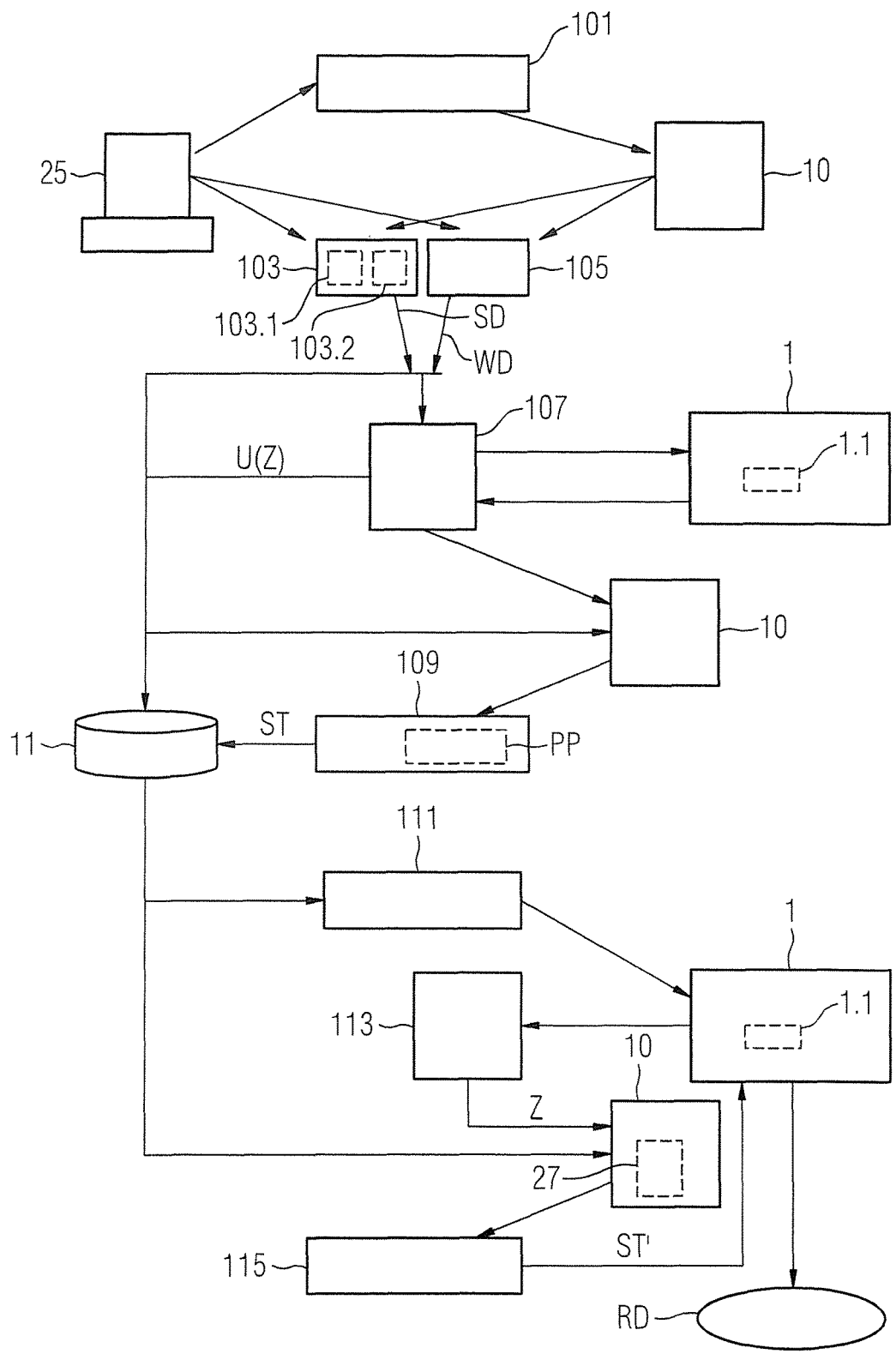
FIG. 2 is a flowchart illustrating the method according to the invention.

FIG. 2 shows a method according to the invention for the operation of a medical imaging examination apparatus having multiple subsystems and a control computer 10 that controls the subsystems in a coordinated manner in order to carry out a scan sequence.

For this purpose, before the start of a scan to be performed on a patient P or other examination object, in step 101, the control protocol assigned for a scan to be carried out is first transferred to the control computer 10 of the medical imaging examination apparatus 1. For this purpose, inputs can be made by a user at the terminal 25 of the medical imaging examination apparatus 1, e.g. a particular control protocol selected and/or adjusted according to current wishes, as described above.

In step 103, the sequence control data SD of relevance for the transferred control protocol that define different functional subsequences of a scan sequence belonging to the control protocol are determined and stored in the memory 11. Depending on the type of scan desired, which specifies, for example, the sequence type, further scan parameters and a body region to be examined, namely the control protocol, may be useful for a different selection of sequence control data, e.g. for a dynamic adaptation. For example, if a scan is to be relatively insensitive to variations in the $B_1$ field, in order to simplify the sequence of the subsequent scan, the corresponding sequence control data SD, such as a transmitter scaling for the flip angle setting or $B_1$ shim settings, are arranged as sequence control data SD (step 103.1) to be set statically. This occurs while other sequence control data that concern, for example, the $B_0$ field, are organized as sequence control data SD (step 103.2) to be adapted dynamically. In this way, the robustness of the method can be improved and the scope of the scans to be carried out for determining the ambient conditions can be reduced.

Furthermore, in step 105, different effective volumes WV are assigned to each functional subsequence and stored. This can be done automatically on the basis of the control protocol. E.g. for a desired multi-slice scan, each slice to be recorded can define a volume of this type. Another example is a regional saturation volume pre-determined by the control protocol. Thus, immediately following the setting of the control protocol, a list of all the respective effective volumes WV of relevance during the scan sequence can be created and stored. This will be discussed later below in relation to FIGS. 3 to 5.

It is also possible that changes or enhancements to such a list of effective volumes WV take place automatically on the basis of the imaging sequence selected by the control protocol. This is conceivable particularly in cases where for reasons of MR physics, e.g. for avoiding artifacts, e.g. "inflow" when using magnetization inversion techniques or "chemical shift artifacts" in cases of regional saturation, such corrections of the parameters given by the user in the form of the control protocol are necessary. It is also conceivable that the scan sequence selected by the control protocol requires internally, i.e. without an associated parameter that is manipulable by a user, further volumes for special manipulations of the spin system and these are therefore recorded as effective volumes WV.

Furthermore, a direct, or even only an indirect, manipulation of optimization volumes can be provided by the user. For example, the user can specify a volume as an optimization volume (e.g. a "volume of interest") which, for example, includes the anatomical region that is of interest. The respective effective volumes WV can then each be restricted to the subregion of the overlap itself with the applicable optimization volume. Thus, the method according to the invention enables optimization for any desired subregions of the effective volume and is not restricted, for example, to the effective volumes pre-determined by the scan, as in the case of slices in multi-slice scans.

In step 107, the current ambient conditions U(Z) of the medical imaging examination device 1 that are decisive for the determined relevant sequence control data SD and associated effective volumes WV are determined for a series of states Z of physiological processes that occur during the scan sequence. For this purpose, for example, for all states of the observed physiological processes expected during a scan, the corresponding ambient conditions can be determined.

If the physiological process observed is the breathing, then, for example, for the states "exhaled" and "inhaled" and possibly also for further "intermediate states" between these "extreme states" of the breathing, the ambient conditions can be determined. The same applies for other periodically recurring physiological processes. The number of states per observed physiological process can be selected, for example, taking account of the scan, particularly the temporal timing of the scan and, for example, a mean repetition duration for periodically recurring physiological processes such as the breathing or the heartbeat or artificially performed periodic movements, for example, at a joint of a patient under investigation, and/or taking account of existing interpolation and/or simulation processes with which "missing" states can be subsequently calculated.

For non-periodic physiological processes as well, for example voluntary or involuntary movements of a patient to be examined, ambient conditions can be determined for different states of such a process. For example, upon a movement of a body part of the patient, such as the head or an arm or leg, the body part can be brought into different states (positions) that are expected, in order to determine the ambient conditions in each case.

The determination of the ambient conditions for the various states of an observed physiological process can be carried out during the unhindered progression of the physiological process, e.g. during free breathing or free movement (particularly following a request to the patient). The states to be associated with a particular ambient condition can be determined with the use, e.g., of rapid scan methods, such as by simple and rapidly recordable navigators, directly by the medical examination apparatus (scanner), or with the use of suitable external sensors such as a breathing belt, pulse sensor, ECG, etc.

It is also or alternatively conceivable to undertake the determination of the ambient conditions for the different states of a physiological process being observed at fixed states, e.g. by breath holding techniques or fixing a movement state for a determination of the ambient conditions. Again, suitable external sensors for determining the states can be used or the states can be determined directly by the medical examination apparatus, wherein with fixed states, more complex (and possibly more accurate) measuring methods can also be used for determining the states, particularly since more time can be used for the determination thereof.

The determination of the states of physiological processes for which the ambient conditions are determined can thus be undertaken during the unhindered progress of the physiological processes or at fixed individual states of the physiological processes.

The determination of the decisive ambient conditions can be done in reliance on the associated effective volumes WV and the determined required control sequence data SD, and their division into statically recordable data 103.1 and dynamically adaptable sequence control data 103.2. The division of the determined sequence control data SD defines for which physical ambient conditions U a global value is sufficient (with statically applicable sequence control data), and when local values are required for the ambient conditions U (for sequence control data that are to be adapted dynamically). For global values, generally, a rapidly executable adjustment scan with the medical imaging examination apparatus 1 is sufficient. For local values, under some circumstances, more extensive adjustment scans are required. For example, local values of the ambient conditions U can be determined by successive adjustment scans for each relevant effective volume WV or the relevant subregion of the effective volume. This methodology represents a simple and established method, although it is time-consuming and must be repeated if the sequence control data are altered. Due to the restriction to adjustment scans only for the sequence control data relevant for the respective control protocol, however, the number of adjustment scans to be carried out and thus the outlay are further limited. Alternatively, such as in a one-time procedure, maps of the physical ambient conditions U are recorded, which can then serve as a database for any desired sequence control data SD. For example, for this purpose, maps of the B0 field distribution and/or maps of the B1 field distribution are recorded, the latter, if required, for a plurality of or even all elements of a transmitting system comprising a number of transmitting elements. Herein, in both cases, established adjustment scans are used. If ambient condition data are available for relevant effective volumes WV or relevant subregions of the effective volumes from earlier adjustment scans, these can continue to be used without renewed adjustment scans. Thus adjustment data, once recorded, are usable like, for example, previously determined ambient conditions for particular relevant effective volumes WV or relevant subregions of the effective volumes, for a number of scans.

In the control computer 10, in step 109, control signals ST for the scan sequence are calculated based on the sequence control data SD determined, the associated effective volumes WV and the decisive current ambient conditions U determined per observed state, and are stored in the memory 11. Control signals ST are therefore available for all the observed states of observed physiological processes. The calculation takes place such that the functional subsequences of the scan sequence are optimized locally at least with regard to a subregion of the associated effective volume WV thereof, for example the intersection region of the respective effective volume with an optimization volume.

In the calculation of the control signals ST, a plausibility check PP can also be included in order to determine any faults as early as this stage at a central site and thus to be able to catch them. For example, the plausibility check PP can place control signals ST calculated for different effective volumes WV in relation to one another. In this context, interactions between different sequence control data, e.g. between gradient non-linearities, RF center frequencies, and shim currents, can be taken into account. Since the calculation of the control signals ST for the entire scan is carried out before the start of the scan taking account of the scan protocol, mean values, in particular SAR values and stimulation potentials, can be considered.

Additionally or alternatively, the calculated control signals for different effective volumes WV or their desired subregions can be placed in relation to one another in order to be able to correct any erroneously calculated control signals. For this purpose, it can be taken into account, for example, that real physical ambient conditions typically have only a moderate spatial variation and this should also apply for the optimized calculated control signals. If this is not the case, this could lie in a lack of quality of the associated measured ambient condition data underlying the calculation. Such control signals ST calculated on a faulty basis can be discovered in the plausibility check PP and replaced, for example, with corrected control signals interpolated from the corresponding control signals ST of adjacent effective volumes WV.

Furthermore or alternatively, the plausibility check PP can cover threshold values to be adhered to for the sequence control data SD, which ensure, for example, that the limits pre-determined by the medical imaging examination apparatus 1, e.g. for technical reasons, for the respective sequence control data SD, such as gradient currents (maximum or average permissible current in the gradient coils) and hence slew rates or first-order shim currents (average permissible offset current in the gradient coils) and shim currents of higher order (average permissible current in the shim coils), maximum offset frequencies of the RF transmission and receiving system, e.g. for the RF center frequencies, etc. are not exceeded.

Apart from system-related threshold values of this type, safety-related threshold values can also be provided which restrict, for example, the SAR loading applied by the scan, for example, a maximum or mean permissible RF transmission power, particularly in multi-channel transmission systems.

Furthermore or, as an alternative, quality-related threshold values can be provided which ensure, for example, that by the optimization, a control signal does not deviate in a quality-impairing manner from the values originally pre-determined in the control protocol. For example, an RF center frequency deviating, due to the optimization, in a faultily severe manner from the originally intended RF center frequency could lead thereto that the scanned slice or the scanned extract in the examination object is displaced and that therefore the desired region in the examination object is not scanned (e.g. another or a displaced anatomy of the patient P is imaged).

In the case of a scan with an exclusively static adaptation of the sequence used, wherein only one effective volume thus exists in which the subsequences are optimized, typically there remains sufficient time for intensive checking of the results so that with displaced scans, if required, renewed scanning with corrected values can be performed.

In the case of scans with dynamic adaptation of the sequence control data with their plurality of effective volumes, such a renewed scan for all effective volumes would mostly be too costly in terms of time. In order therefore to prevent this, as quality-related threshold values, for example maximum deviations of the sequence control data amended by the optimization and contained in the control signal from the value originally provided in the control protocol can be given.

Alternatively, as a quality-related threshold value, a maximum permissible deviation of the parameter dynamically calculated according to the invention can be defined by a corresponding static parameter. Herein, for example, the dynamic variation of the RF center frequency could be restricted to small displacements of the scan volume relative to the size of the region of the examination object to be scanned, for example displacements of less than ten percent, particularly less than five percent, of the size of the region of the examination object to be scanned. The threshold for the displacement can be given by the variation of the RF-center frequency also in pixels, for example "not more than ten pixels" or in a length unit, for example "not more than five millimeters".

It is thus conceivable, for example, to transmit all the sequence control data to be set dynamically from step 103, the associated effective volumes from step 105 and the determined ambient conditions from step 107 to the control computer 10 that, taking account of the scan sequence belonging to the selected scan in step 109, determines the system control data. For example, the temporal sequence of gradient pulses to be switched can be calculated, taking account of volume-specific shim offset currents in the plausibility check PP and/or the temporal sequence of RF pulses, taking account of volume-specific transmitter scaling factors and/or RF power distributions of the RF transmission system in the plausibility check PP. A calculation for a representative portion, e.g. a repetition of the scan sequence, can suffice. From the temporal succession of hardware-control-sequence control data, the mean values of the relevant variables can be determined, e.g. the mean thermal load caused by the gradient currents or the mean RF power. From the temporal succession of RF-specific sequence control data, the prognosticized energy input into the examination object can be determined, possibly using known models. From the temporal succession of gradient-specific sequence control data, the predicted stimulation potential can be calculated using known models. During scans with physiological triggering, at least estimated values can also be determined, e.g. for a worst case scenario. Apart from simple mean values, more complex variables, for example, account models as described in DE 10 2007 036564 B4 can also be considered.

If a quality-related threshold value is found during the plausibility check PP to be exceeded, then, for example, either the quality-related threshold value itself or the static value can be used as the corrected value or scan pauses can be introduced into the scan sequence. For example, the repetition time TR can be extended so as to reduce the variables affected by the exceeded threshold value. It is also conceivable to reduce the flip angle to be reached and/or to adjust the RF pulse types (e.g. by extending the RF pulse duration or using "low-SAR" or verse pulses) in order, for example, to reduce SAR-relevant variables and in this way to return again within the limit region pre-determined by the relevant threshold value. Similarly, the minimum gradient rise time can be increased or the selected image portion (FOV) can be enlarged or the matrix size of the scan can be reduced, in order to reduce the values of simulation limit-relevant sequence control data and to bring them again within the limits pre-determined by the respective threshold values.

Instead of a direct use of the static value of such a value to be corrected, the calculated value in question can also be approximated, e.g. in steps, to the static value until it is within the limits set by the associated threshold value. In addition or alternatively, the user can be informed via the terminal 25 regarding the exceeding of the quality-related threshold value and, if required, regarding changes made as a consequence. In SAR-related cases, following confirmation by the user, a change into another SAR control mode or stimulation control mode is undertaken. Thereby, the reaction to such cases of exceeding threshold values are made explicable to a user. The stated types of threshold values can be combined as desired for different system control data.

Thus, by the use of such threshold values, system-related or subject-related limitations can be dealt with by the method. Thus, scan interruptions are effectively prevented in the scan following the calculation of the sequence control data, since exceeding of technical or physiological limits cannot occur whilst, at the same time, the efficiency of the medical imaging examination apparatus can be optimally utilized.

If the plausibility check PP detects any lack in the calculated control signals ST, for example, the user can be notified by means of the terminal 25 and, if required, alternative solutions are offered and/or selected. If calculated sequence control data are corrected during the plausibility check PP, the corrected value is stored in the memory 11.

Nevertheless, the central control computer 20 of the control computer 10 can include, apart from a control signal generating module 21, a sequence control data determining module 22 that recognizes and reads out the sequence control data SD within a control protocol SP. In addition, the central control computer 20 preferably includes a position data determination module 23 that recognizes the effective volume position data PD in the control protocol SP, and the thereby obtained sequence control data and position data are then processed in a suitable manner by the control signal generating module 21 in order to achieve the desired optimization. In principle, the sequence control data determination module 22 and the position data determination module 23 can also be realized as a combined module which recognizes the sequence control data SD and the effective volume position data PD and transfers them to the control signal generating module 21. Furthermore, the sequence control data determination module and the position data determination module can also be integrated into the control signal generating module 21. In FIG. 1, however, a separate representation of these modules was selected in order to make clear that the optimization for the effective volumes associated with the individual subsequences of the scan sequence only takes place fully automatically in the central control computer 20.

The position data calculation device 23 can also be configured so that it determines a restricted optimization volume for individual subsequences, for example, on the basis of effective volume position data PD obtained and image data DB generated with the use of the reconstruction unit 13 in previous scout scans.

An example of when this is useful is also shown schematically in FIG. 1 on the patient P in the patient tunnel 3. Shown here are three different slices for which particular subsequences are to be carried out within a scan sequence. Each of these slices has a quite particular effective volume $WV_1$, $WV_2$, $WV_3$, wherein however, only part of this volume actually includes part of the patient P to be examined. Regions in this effective volume $WV_1$, $WV_2$, $WV_3$ outside the patient's body do not contain any essential image information. It is therefore useful to use as the optimization volume only the subregion of the effective volume $WV_1$, $WV_2$, $WV_3$ which overlaps the body of the patient P. In the case of the third slice $WV_3$, this optimization volume $OV_3$ is the whole region which results as the overlap between the effective volume $WV_3$ and the volume of the patient's body.

Based on the other two effective volumes $WV_1$, $WV_2$, a further variant is shown. It is herein assumed that a particular organ O is to be examined as the examination object O within the body of the patient P. This organ O has a particular object volume OV. Since only this volume OV is of interest, the overlap of the object volume OV with the effective volumes $WV_1$, $WV_2$ is formed in order to find the respective optimization volumes $OV_1$, $OV_2$. If the case should arise that an effective volume does not have any overlap with an associated optimization volume, for example, the formation of the overlap can be dispensed with and only the effective volume considered or the optimization volume for the associated effective volume having no overlap with the optimization volume can be extrapolated as the new optimization volume to be taken as the basis. A case of this type could arise, for example, if the slices provided for the scan are larger than the VOI stipulated by the user or are larger than the organ to be imaged.

When the actual scan is now started (step 111) according to the control protocol, the control computer 10 uses the stored control signals ST for the scan. During the ongoing scan, in a step 113, at least one current state of the physiological processes observed is determined and the control signals ST' used for the current scan are determined in a step 115 in the control computer 10 on the basis of the stored control signals (ST) taking account of the at least one current state. Herein, in each case, for example, a stored control signal ST belonging to a current effective volume of the ongoing scan, possibly adjusted following the plausibility check PP and matching the current state is loaded from the memory 11 and used to control the scan. It is also conceivable that the stored control signals ST are not used directly, but serve only as the basis for the control signals used, as described below.

For example, during the scan, the current effective volume of the scan sequence can always be determined. For the current effective volume, a control signal to be used can be determined from the stored control signals. It is possible for the actually used control signals to be interpolated on the basis of the stored control signals and the associated stored effective volumes, ambient conditions and states of the physiological processes according to the effective volumes and/or ambient conditions existing during the scan.

The determination of the current states can take place in the same way as the determination of the states of the physiological processes for which the ambient conditions have already been determined in step 107 before the start of the scan in step 111. In this way, it can be ensured that the current states and the already stored states already inherently have the greatest possible similarity. Thus, the current states of the observed physiological processes can be determined, as described above in relation to step 107, by suitable measuring methods, e.g. navigators or more complex scan methods, by the medical examination apparatus 1 and/or by suitable external sensors 1.1, such as a breathing belt or the like, pulse sensors or ECGs, etc.

In step 115, those stored control signals ST which were calculated on the basis of at least one state which is or are the most similar to the at least one current state, can become control signals ST' to be used for the current scan.

It is also possible, in step 115, to determine the control signals ST' to be used for the ongoing scan, by interpolation and/or by means of simulation methods, from the stored control signals ST. In a simulation of this type, in particular, simulations that simulate the field distributions of the basic magnetic field and/or of the radio frequency field during the movement of tissue are possible. In a simple exemplary embodiment, a linear interpolation can be used as such an interpolation. If, for example, for the states Z=1 and Z=3 (e.g. 1="inhaled" and 3="exhaled") optimized control parameters are calculated for a particular effective volume, e.g. the center frequencies F(Z=1)=F1, F(Z=3)=F3, then suitable control parameters for intermediate states such as Z=2 can be interpolated, e.g. by the equation F(Z=2)=(F1+F3)/2.

It is also possible to use a synchronization unit 27 included, for example, within the control computer 10, which controls when, following determination of a change in the at least one current state, the control signals ST' that are used are adapted. This can be useful, in particular, if the time point at which the control signals ST, ST' are adapted following a detected change in the states of the observed physiological processes and thus in the ambient conditions underlying the control signals ST' is not an arbitrary time point. The synchronization unit 27 controls the adaptation of the control signals taking account of the ongoing scan, particularly such that an adaptation of the control signals has no negative effects on the scan data acquired. By such synchronized updating of the control signals used, the data consistency can be improved.

The control signals ST, ST' control the medical imaging examination apparatus 1, which thereby generates raw data RD which again is stored in the memory 11 or is reconstructed as image data or spectroscopic data and, if required, can be displayed.

With reference to FIGS. 3 to 5, the possibilities for optimizing the individual subsystems to an effective volume associated with a particular subsequence will now be described, again using an actual but highly simplified scan sequence MS.

In the uppermost line, various subsequences $TS_1$, $TS_2$, ..., $TS_8$ are named, in each case in the form of individual blocks. Shown in the bottom line are the effective volumes $V_1$, $V_2$, $V_3$, $V_4$ associated with these subsequences $TS_1$, $TS_2$, ..., $TS_8$ of the scan sequence MS.

It is apparent that the first subsequence $TS_1$ is associated with a first effective volume $V_1$ and the second subsequence $TS_2$ is associated with a second effective volume $V_2$. A common effective volume $V_3$ is associated with the subsequences $TS_3$, $TS_4$, $TS_5$. Also, an effective volume $V_4$ is associated with the subsequences $TS_6$, $TS_7$, $TS_8$.

Shown between the bottom and upper lines, each on separate time lines for the individual subsequences, are the pulses to be output by the subsystems. I.e. by the synchronous output of the pulses, each shown beneath the subsequences $TS_1$, $TS_2$, ..., $TS_8$ marked by the blocks or the setting of the corresponding parameters at the subsystems, the individual subsequences $TS_1$, $TS_2$, ..., $TS_8$ are carried out. In the second to top line, the radio frequency pulse forms and amplitudes to be output by the radio frequency pulse amplifier RFPA are shown symbolically. In the second line, the NCO phase to be set in each case is symbolized, wherein the gradient of the curve symbolizes the frequency size. In the following lines, the gradient pulses Gx, Gy, Gz are shown and in the last but one line, the readout windows in which an analogue/digital converter ADC for reading out a selected receiving coil is controlled. For the sake of simplicity, a single-channel transmitting system is represented here. In multi-channel systems, for example, for every transmitting element, the RF pulse sequence (amplitude and/or phase) could look different in order to realize the B1 shim.

The first subsequence $TS_1$ of the scan sequence MS serves here for regional saturation, i.e. all the nuclei within a regionally limited effective volume $V_1$ are saturated. For this purpose, initially for dephasing, short intensive Gx and Gy gradients are switched. Subsequently, a radio frequency pulse of a particular form and amplitude with a particular temporally variable phase sequence output by the NCO is emitted, the rise of said pulse corresponding to the frequency of the radio frequency pulse, whilst simultaneously for slice selection, a further Gy gradient pulse is emitted. This subsequence concludes with a further short intensive gradient pulse in the x- and y-directions for dephasing.

With regard to the effective volume $V_1$, different parameters can be optimized automatically by the control device, since this effective volume $V_1$ is known. Firstly, the amplitude A of the radio frequency pulse to be emitted and simultaneously also the frequency F which is output by the NCO are optimized. In addition, for example, the shim offset currents S for the gradient coils Gx, Gy are suitably set and equally suitable parameters for a Maxwell correction M can also be transferred. The parameters locally optimized depending on the respective effective volume $V_1$ are shown in FIG. 3 with arrows starting from the bottom line and from the first volume $V_1$.

A further subsequence $TS_2$, which directly adjoins the first subsequence $TS_1$, is a chemical saturation, for example, a fat saturation. This takes place very similarly to the regional saturation by emitting a radio frequency pulse at a particular amplitude and a frequency pre-determined by the NCO, wherein here the frequency is higher than with the regional saturation in the subsequence $TS_1$. Here also, before the emission of the radio frequency pulse and after the emission of the radio frequency pulse, in each case, only the dephasing pulse is switched in the Gx and Gy gradient. The emission of a Gy gradient for slice selection (as in the first subsequence $TS_1$) does not take place since the saturation is to take place globally, i.e. the effective volume $V_2$ is here the whole volume in the scanning space. FIG. 4 shows how, for example, in this subsequence $TS_2$, the amplitude A and the frequency F are optimized for the current effective volume $V_2$.

Following this chemical saturation $TS_2$, the actual recording of raw data then takes place for a first slice by means of three subsequences $TS_3$, $TS_4$, $TS_5$, which must all act on the relevant slice. This slice determines the associated effective volume $V_3$. The first subsequence $TS_3$ serves for slice excitation in the effective volume $V_3$. This is achieved by emitting a radio frequency pulse RF with a particular amplitude and a frequency pre-set by the NCO with simultaneous emission of a Gz slice gradient pulse and a subsequent shorter, negative Gz rephasing pulse. The next subsequence $TS_4$ serves for phase encoding. For this purpose, merely a Gy gradient pulse is switched. In the subsequent subsequence $TS_5$, the reading out of the magnetic resonance signals generated in the effective volume $V_3$ takes place in that initially a negative Gx gradient pulse is emitted for dephasing and subsequently a positive Gx gradient pulse is emitted for rephasing, wherein simultaneously, the ADC is activated for reading out. Thereafter, the scanning of this slice is ended. Optimizable parameters are shown again in FIG. 5 by arrows: the amplitude A of the emitted radio frequency pulse, the phase and frequency F of the NCO set on output of the radio frequency pulse, and again the parameters for the shim offset S and the Maxwell correction parameters M on switching the gradient pulses Gx, Gy, Gz, respectively. With regard to the ADC, an optimization can be carried out in that—provided different readout coils (e.g. a number of local coils) are available—the best coil combination is selected for the relevant effective volume $V_3$, and this is symbolized by the coil selection parameter C.

Subsequently to the subsequence $TS_5$ with which the data are read out of the volume $V_3$, excitation of a further slice can take place within the subsequence $TS_6$. This further slice is represented here by the effective volume $V_4$. In the same way as for the first slice, i.e. for the effective volume $V_3$, in order to determine the image data also for the effective volume $V_4$, a subsequence $TS_7$ for phase encoding and a further subsequence $TS_8$ for reading out the slice are carried out.

It is clear that, in the same manner, further slices can be read out, wherein corresponding subsequences must be repeated. Similarly, in any desired manner, including between the scanning out of slices, further saturation subsequences or other special subsequences can be inserted, for example, to label or mark blood or other fluids, the flow of which in the body is to be determined later. According to the multiple highly varied possible subsequences and associated effective volumes, there arise also the most varied of possibilities for optimizing parameters of the different subsystems for the individual subsequences in view of the associated effective volumes.

Although modifications and changes may be suggested by those skilled in the art, it is the intention of the inventors to embody within the patent warranted hereon all changes and modifications as reasonably and properly come within the scope of their contribution to the art.

We claim as our invention:

1. A method for operating a medical imaging examination apparatus comprising a plurality of apparatus subsystems, comprising:

providing a control protocol to control computer that is assigned to a scan sequence in which said control computer will control the plurality of apparatus subsystems in coordination to conduct the scan sequence to acquire medical imaging data from an examination subject;

in said control computer, determining sequence control data for said control protocol that define different functional sub-sequences of said scan sequence to be performed respectively by said apparatus subsystems;

in said control computer, assigning respectively different effective volumes of the examination subject to the respective functional sub-sequences;

in said control computer, determining ambient conditions of said medical imaging examination apparatus that affect said sequence control data and said effective volumes for each of a series of physiological states of the examination subject;

in said control computer, calculating and storing control signals for said scan sequence, for each of said states, dependent on said determined sequence control data, the determined effective volumes, and the determined ambient conditions, by executing an algorithm in said control computer that optimizes the functional sub-sequences locally in the examination subject at least with regard to a sub-region of the respective effective volumes; and in said control computer, starting said scan sequence using the stored control signals and, during said scan sequence, providing said control computer with a designation of at least one current state of said physiological states and automatically modifying said control signals for a remainder of said scan sequence, dependent on said at least one current state.

2. A method as claimed in claim 1 comprising determining said state of said physiological processes for which said ambient conditions are determined in a same way as said current state during said scan sequence.

3. A method as claimed in claim 1 comprising detecting said at least one current state of said physiological processes during said scan sequence using a medical examination apparatus that is also operated to execute said scan sequence.

4. A method as claimed in claim 1 comprising detecting said at least one current state of said physiological processes during said scan sequence with at least one sensor that is external of the examination object.

5. A method as claimed in claim 1 comprising determining said states of said physiological processes from which said ambient conditions are determined during an unhindered progression of said physiological processes in said examination object.

6. A method as claimed in claim 1 comprising determining said states of said physiological processes from which said ambient conditions are determined at fixed respective states of the individual physiological processes.

7. A method as claimed in claim 1 comprising adapting said control signals during said scan sequence dependent on said at least one current state by using a control signal, among said stored control signals, that was determined for respective states of said physiological processes that is most similar to said at least one current state.

8. A method as claimed in claim 1 comprising adapting said control signals during said scan sequence by interpolating control signals among said storage control signals.

9. A method as claimed in claim 1 comprising adapting said control signals during said scan sequence by executing a simulation algorithm in said control computer starting from said stored control signals.

10. A method as claimed in claim 1 comprising, in said control computer, executing a synchronization algorithm upon a detected change in said at least one current state in said scan sequence.

11. A method as claimed in claim 1 comprising, in said modifying of said control signals, implementing a plausibility check to determine whether an adapted control signal is acceptable for use in said remainder of said scan sequence.

12. A medical imaging examination apparatus comprising:

a plurality of apparatus subsystems;

a control computer provided with a control protocol that is assigned to a scan sequence in which said control computer is configured to control the plurality of apparatus subsystems in coordination to conduct the scan sequence to acquire medical imaging data from an examination subject;

said control computer being configured to determine sequence control data for said control protocol that define different functional sub-sequences of said scan sequence to be performed respectively by said apparatus subsystems;

said control computer being configured to assign respectively different effective volumes of the examination subject to the respective functional sub-sequences;

said control computer being configured to determine ambient conditions of said medical imaging examination apparatus that affect said sequence control data and said effective volumes for each of a series of physiological states of the examination subject;

said control computer being configured to calculate and store control signals for said scan sequence, for each of said states, dependent on said determined sequence control data, the determined effective volumes, and the determined ambient conditions, by executing an algorithm in said control computer that optimizes the functional sub-sequences locally in the examination subject at least with regard to a sub-region of the respective effective volumes; and said control computer being configured to start said scan sequence using the stored control signals and, during said scan sequence, receive a designation of at least one current state of said physiological states and automatically modify said control signals for a remainder of said scan sequence, dependent on said at least one current state.

13. A medical imaging examination apparatus as claimed in claim 12 wherein said plurality of apparatus subsystems form a magnetic resonance scanner.

14. A non-transitory, computer-readable data storage medium encoded with programming instructions, said storage medium being loaded into a control computer of a medical imaging examination apparatus comprising a plurality of apparatus subsystems, said programming instructions causing said control computer to:

receive a control protocol that is assigned to a scan sequence in which said control computer will control the plurality of apparatus subsystems in coordination to conduct the scan sequence to acquire medical imaging data from an examination subject;

determine sequence control data for said control protocol that define different functional sub-sequences of said scan sequence to be performed respectively by said apparatus subsystems;

assign respectively different effective volumes of the examination subject to the respective functional sub-sequences;

determine ambient conditions of said medical imaging examination apparatus that affect said sequence control data and said effective volumes for each of a series of physiological states of the examination subject;

calculate and store control signals for said scan sequence, for each of said states, dependent on said determined sequence control data, the determined effective volumes, and the determined ambient conditions, by executing an algorithm that optimizes the functional sub-sequences locally in the examination subject at least with regard to a sub-region of the respective effective volumes; and start said scan sequence using the stored control signals and, during said scan sequence, receive a designation of at least one current state of said physiological states and automatically modify said control signals for a remainder of said scan sequence, dependent on said at least one current state.

* * * * *